(12) United States Patent
Glinec et al.

(10) Patent No.: US 10,076,391 B2
(45) Date of Patent: Sep. 18, 2018

(54) METHOD AND SYSTEM FOR BITE REGISTRATION

(71) Applicant: Carestream Dental Technology Topco Limited, London (GB)

(72) Inventors: Yannick Glinec, Montevrain (FR); Qinran Chen, Shanghai (CN); Mo Yufeng, Shanghai (CN)

(73) Assignee: Carestream Dental Technology Topco Limited, London (GB)

( * ) Notice: Subject to any disclaimer, the term of this patent is extended or adjusted under 35 U.S.C. 154(b) by 143 days.

(21) Appl. No.: 14/770,177

(22) PCT Filed: Mar. 11, 2013

(86) PCT No.: PCT/CN2013/072420
§ 371 (c)(1),
(2) Date: Aug. 25, 2015

(87) PCT Pub. No.: WO2014/139078
PCT Pub. Date: Sep. 18, 2014

(65) Prior Publication Data
US 2016/0008116 A1   Jan. 14, 2016

(51) Int. Cl.
G06K 9/00 (2006.01)
A61C 19/05 (2006.01)
G06T 19/20 (2011.01)
A61C 9/00 (2006.01)
A61C 7/00 (2006.01)

(52) U.S. Cl.
CPC ............ *A61C 19/05* (2013.01); *A61C 7/002* (2013.01); *A61C 9/0053* (2013.01); *G06T 19/20* (2013.01); *G06T 2219/2004* (2013.01)

(58) Field of Classification Search
CPC ....... A61C 19/05; A61C 7/002; A61C 9/0053; G06T 19/20; G06T 2219/2004
See application file for complete search history.

(56) References Cited

U.S. PATENT DOCUMENTS 7,118,375 B2   10/2006   Durbin et al.
2002/0015934 A1   2/2002   Rubbert et al.
(Continued)

FOREIGN PATENT DOCUMENTS

CN   101228556   7/2008
DE   102010040096   3/2012
(Continued)

OTHER PUBLICATIONS

Sirona. "CEREC SW Operator's Manual Software Version 4.0." Aug. 2012.*
(Continued)

*Primary Examiner* — Nirav G Patel

(57) ABSTRACT

The present invention relates to method and system for bite registration using multiple bite registrations. In this method or system, when both the 3D teeth model of the upper jaw and the 3D teeth model of the lower jaw are successfully aligned with the bite surface, the bite surface with the 3D teeth models of the upper jaw and the lower jaw is displayed for further evaluation; the bite surfaces selected by the user are combined to generate a final bite registration. Using multiple bite surfaces for registration improves the accuracy.

21 Claims, 8 Drawing Sheets

(56) References Cited

U.S. PATENT DOCUMENTS

2002/0094509 A1 7/2002 Durbin et al.
2010/0151404 A1* 6/2010 Wu .......................... A61C 7/00
433/24

FOREIGN PATENT DOCUMENTS

EP 2428764 3/2012
JP 5017487 B 9/2012
WO 2012096312 7/2012

OTHER PUBLICATIONS

International Search Report, dated Dec. 19, 2013 International Application No. PCT/CN2013/;072420, 5 pages.
EP Search Report, dated Oct. 27, 2016, EP Application No. 13878438, 3 pages.

\* cited by examiner (a)

(b)

METHOD AND SYSTEM FOR BITE REGISTRATION

CROSS REFERENCE TO RELATED APPLICATIONS

This application claims the benefit of and is a U.S. National Phase filing of PCT Application PCT/CN2013/072420 filed Mar. 11, 2013 entitled "METHOD AND SYSTEM FOR BITE REGISTRATION", in the name of Glinec et al.

FIELD OF THE INVENTION

The present invention relates to the technical field of dental 3-dimensional (3D) imaging, and in particular to a method and computerized system for bite registration using at least two bite surfaces.

BACKGROUND

In dental field, it is one of key points to obtain an accurate 3D teeth model corresponding to clenched state during the course of treatment (for example, orthodontics). 3D camera system is used to create a 3D model of the teeth directly with the patient, which avoids the need to cast impressions and send them to the lab for restoration. This reduces cost and simplifies the workflow of dental restoration.

For the process of constructing global 3D teeth model, the step of bite registration is one of necessary and crucial steps. Bite registration is the process of registering the upper jaw with the lower jaw, which could establish a 3D spatial positioning relationship between an upper jaw and its corresponding, lower jaw in clenched state.

In an existing 3D camera system, during bite registration, only one bite surface is required for constructing a global 3D teeth model. In this method, the single bite surface is captured from one certain location (such as right side of molars) of the clenched teeth by a scanner, then the 3D teeth models of the upper jaw and the lower jaw captured independently are stitched onto the bite surface in a semi-automatic way so as to complete bite registering. However, when the global teeth contains a plurality of teeth (such as more than 5 teeth), the bite registration obtained from only one location of the bite surface may lead to significant mismatch in another location. For example, when only one bite surface corresponding to right side of molars is used, there are several hundreds microns of mismatch in the bite registration corresponding to the distant end (such as incisors or left side of molars). Thus, it is difficult to ensure the overall accuracy of bite registration, which results that a great difference may exist between the ultimate virtual global 3D teeth model constructed by this single bite registration and the actual global teeth in unique clenched state.

U.S. Pub. No.: US 2005/0196724A1 to Ross J. Miller et al. discloses a device for bite registration, which uses block (200) filled with impression material to record bite configurations. Evidently, it can not provide digital visual bite surface, and thus is not adaptable to digital 3D camera system.

Further, U.S. Pat. No. 8,121,718 B2 to Rüdger Rubbert et al, discloses an interactive orthodontic care system based on intra-oral scanning of teeth. In this system, when stitching both the upper jaw and the lower jaw onto the bite surface, it is completed in a manual way. Moreover, only one bite surface is used for obtaining a 3D virtual model of the teeth either.

SUMMARY OF THE INVENTION

In view of above problems, the object of the present invention is to improve the accuracy of bite registration, at least.

In order to realize the above object or other objects, the invention provides the following technical solutions.

According to one aspect of the invention, a method of bite registration is provided, this method comprises the steps of:
  a. generating 3-dimensional (3D) teeth models of the upper jaw and the lower jaw;
  b. acquiring a bite surface containing a portion of upper and lower jaws simultaneously;
  c. attempting to align the 3D teeth models of the upper jaw and the lower jaw with the bite surface;
  d. displaying the bite surface together with the 3D teeth models of the upper jaw and the lower jaw aligned with the bite surface if alignment is successful;
  e. repeating step b to step d so as to obtain at least two successful bite registrations corresponding to different displayed bite surfaces;
  f. selecting one or more successful bite registrations by evaluating at least two successful bite registrations; and
  g. computing a final bite registration using selected one or more successful bite registrations.

According to another aspect of this invention, a system for bite registration is provided which includes:
  means for generating 3D teeth models of the upper jaw and the lower jaw;
  means for acquiring a bite surface containing a portion of upper and lower jaws simultaneously;
  means for attempting to align the 3D teeth models of the upper jaw and the lower jaw with the bite surface;
  means for displaying the bite surface together with the 3D teeth models of the upper jaw and the lower jaw aligned with the bite surface if alignment is successful;
  means for obtaining at least two successful bite registrations corresponding to different displayed bite surface by repeating;
  means for selecting one or more successful bite registrations by evaluating at least two successful bite registrations; and
  means for computing a final bite registration using selected one or ore successful bite registrations.

According to yet another aspect of this invention, a system for bite registration is provided which includes a scanner and a computerized workstation, wherein the workstation is configured as:
  generating 3D teeth models of the upper jaw and the lower jaw;
  acquiring a bite surface containing a portion of upper and lower jaws simultaneously;
  attempting to align the 3D teeth models of the upper and the lower jaw with the bite surface;
  displaying the bite surface together with the 3D teeth models of the upper jaw and the lower jaw aligned with the bite surface if alignment is successful;
  repeating steps acquiring to step of displaying so as to obtain at least two successful bite registrations corresponding to different displayed bite surfaces;
  selecting one or more successful bite registrations by evaluating at least two successful bite registrations; and
  computing a final bite registration using selected one or more successful bite registrations.

BRIEF DESCRIPTION OF THE DRAWINGS

The above and other objects and advantages of the invention will become fully understood from the following detailed description with reference to drawings, in which identical or similar elements are denoted by identical reference signs.

DETAILED DESCRIPTION OF THE INVENTION

Some of the many possible embodiments of the invention will be described below in order to provide a basic understanding of the invention and not to identify crucial or decisive elements of the invention or define the scope of protection. It can be easily understood that according to the technical solutions of the invention, those with ordinary skills in the art can propose other alternative implementations without departing from the true spirit of the invention. Therefore, the following embodiments and accompanying drawings are illustrative description of technical solutions of the invention, and should not be construed as constituting the whole of the invention or as limiting or defining technical solutions of the invention.

Figure 1:
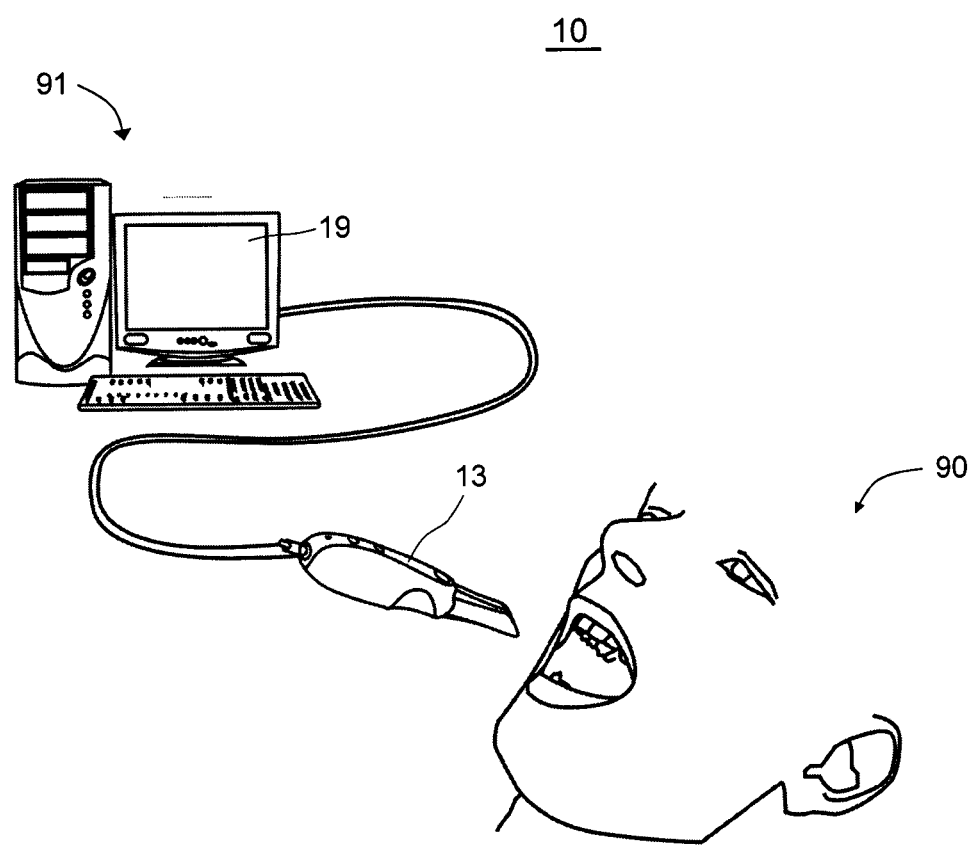
FIG. 1 is a is a schematic structural view of a system for bite registration in accordance with an embodiment of the invention.

FIG. 1 is a schematic structural view of a system for bite registration in accordance with an embodiment of the invention. The system 10 is used to bite registration at least. As simply illustrated in FIG. 1, in this embodiment, the system 10 includes a scanner 13 and a computerized workstation 11. The scanner 13 is handheld by the dentist, and it can be partly put into the mouth of patient 90. When put into the mouth, the scanner 13 can capture image(s) of the teeth or other 3D views as necessary. The scanner 13 and the workstation 11 can be connected in a wireless or wired way so that the images, or views captured by the scanner 13 can be transmitted to the workstation for data processing or real-time displaying. Of course, some instructions generated by the workstation 11 can also be transmitted to the scanner 13 so as to control its action.

The workstation 11 comprises a monitor 19 at least which can display all sorts of 2D/3D images or windows under the control of the workstation 11. Software of bite registration can be installed in the workstation 11. When running the software, the workstation 11 functions as an image processing device which can complete the bite registration step at least in the process of constructing the global 3D teeth model. Of course, it can be understood that the software may not be limited to perform bite registration step but can be used to realize global 3D teeth model in time. Thus, if necessary, the system 10, mainly constituting a 3D camera system adapted for teeth, can also function as constructing the global 3D teeth model of the patient.

The software's function of bite registration is carefully described hereinafter in conjunction with the following figures. Certainly, a method of bite registration can further be applied to construct the global 3D teeth model.

Figure 2:
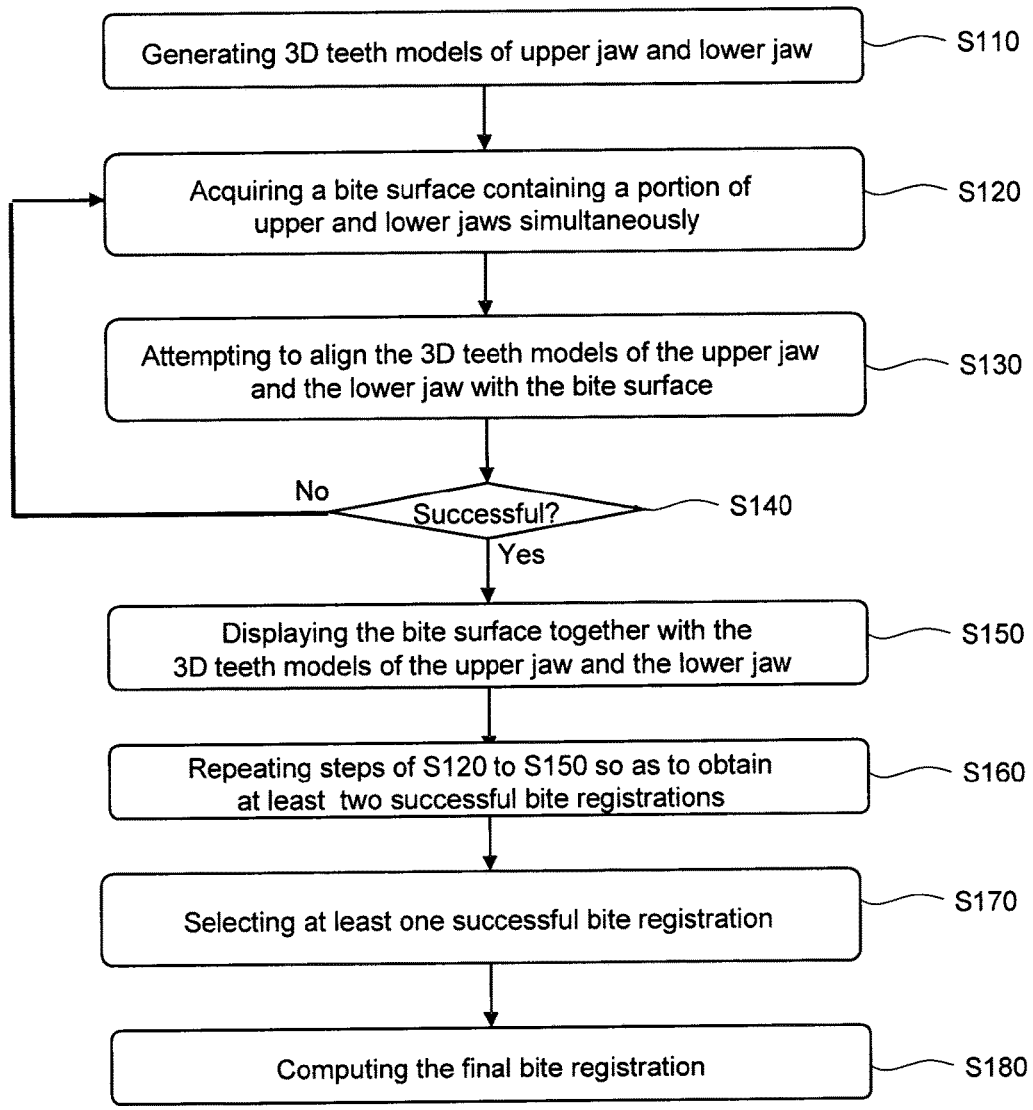
FIG. 2 is a workflow of a method of bite registration in accordance with an embodiment of the invention.

FIG. 2 is a workflow of a method of bite registration in accordance with an embodiment of the invention. In this embodiment, the method in FIG. 2 can obtain at least two successful bite registrations corresponding to different bite surfaces. The following description, conjunction with FIGS. 1-10, describes the workflow of bite registration which obtains at least two successful bite registrations and selects at least one bite registration by user.

Firstly, in step of S110, the dentist operates the scanner 13 in the mouth of the patient 90, thus multiple 2D images of the upper jaw and lower jaw can be respectively captured from different viewpoints. The multiple 2D images are transmitted to the workstation 11, and then are processed so as to generate 3D teeth models of the upper and lower jaws.

Figure 3:
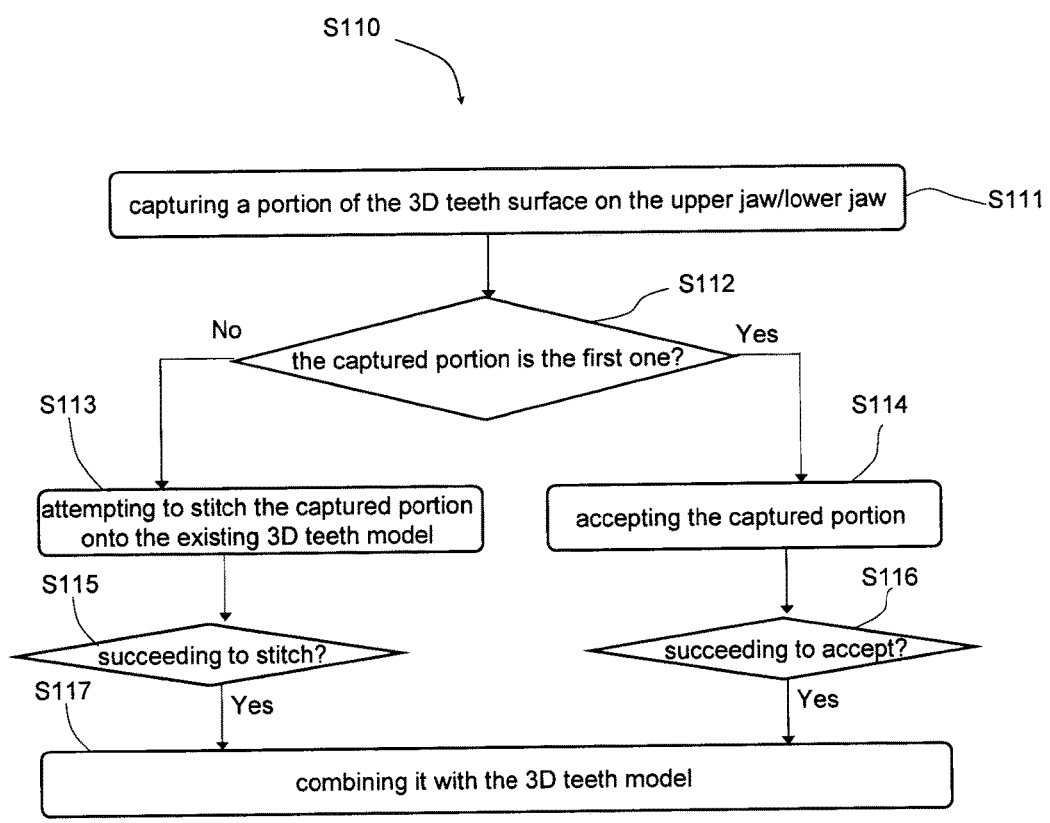
FIG. 3 is a schematic workflow of bite registration in accordance with an embodiment of the invention.
Figure 4:
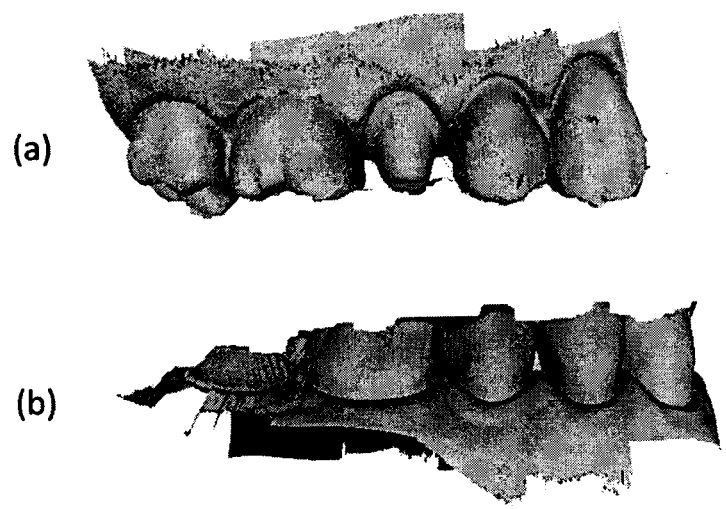
FIG. 4(a) is a 3D teeth models of the upper jaw.
FIG. 4(b) is a 3D teeth models of the lower jaw.

In a preferred embodiment, as shown in FIG. 3, S110 includes the following steps: S111, 3D teeth surface on the upper jaw or lower jaw is captured by the handheld scanner 13; S112, judging whether the captured portion is the first one or not for a certain patient in the workstation 91; S114, if the captured portion is the first one during the scan, the captured portion is accepted; if succeeding to be accepted in S116, entering into S117 of combining the captured 3D teeth surface with the 3D teeth model; S113, if the captured portion is not the first one, attempting to stitch the captured portion onto the existing 3D teeth model; S115 judging whether the captured portion is successfully stitched not if succeeding to stitch in S115, entering into S117 of combining the captured portion with the existing 3D teeth model. Thus, the captured portion combine with the existing 3D teeth model would make the ultimately formed 3D teeth model of the upper or lower jaw more accurate.

In another embodiment, the method of generation of the 3D teeth model in step of S110 can refer to two filed patents of application Ser. No. 13/293,308 and application Ser. No 13/525,590, both with name of "3D INTRAORAL MEASUREMENTS USING OPTICAL MULTILINE METHOD". Those entire contents of these patent applications are incorporated by reference herein.

Figure 5:
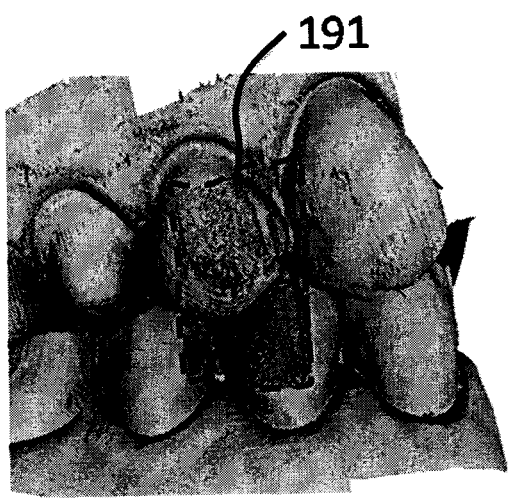
FIG. 5 is a schematic view of bite surface displayed in the monitor.

Further, in step of S120, a bite surface containing a portion of the upper jaw and a portion of the lower jaw simultaneously is acquired. In this embodiment, the scanner 13 is set in a location so as to capture one or more bite views (or surfaces) corresponding to some teeth. The bite view(s) captured by the scanner 13 is (are) obtained in a unique clenched state where the upper jaw is static in relation to the lower jaw. Thus, one or more bite views can form a bite surface containing a portion of upper and lowers jaws simultaneously. In particular, the bite view is a 3D surface containing upper and lowers jaws, and in one embodiment, several bite views corresponding to different teeth respectively can be combined into one view so as to form a bigger bite surface. In one example, the bite surface 191 can be displayed on the monitor in-time as shown in FIG. 5.

It can be understood that the bite surface 191 is a 3D surface, and can be obtained by a method of image processing applied to one or more bite views. In an embodiment, this method is similar with that used in steps of S110. It can also be understood that, since captured in the clenched state, the scanner 13 is convenient to image the outside of the teeth. Thus, the bite surface 191 is a 3D surface usually representing 3D shape characteristic of outside, and it can not substitute the function of the global 3D teeth model obtained ultimately. However, this bite surface can be further used in the process of global matching so as to improve the accuracy of the global 3D teeth model. As the bite surface 191 is also used to align with the 3D teeth models, the bite surface 191 must contain a part of the upper jaw and the lower jaw simultaneously in the unique clenched state.

In a preferred embodiment, the portion of the upper and lower jaws observed in the bite surface can be changed. For example, when repeating to perform step of S120, the bite surface can be obtained from different portions of the clenched upper and lower jaws; thus, the location of the acquired bite surface can be changed. In a selectable embodiment, the obtained bite surface may include, but is not limited to, portions from incisors, premolar, molars.

Further, in step of S130, attempting to align the 3D teeth models of the upper jaw and the lower jaw with the bite surface. In an embodiment, the alignment can be completed at least by stitching of a portion of 3D teeth surface of the bite surface with the 3D teeth models of the upper jaw and the lower jaw. In another embodiment, the alignment can be completed at least by stitching of a portion of 3D teeth surface of the acquired bite surface with either the lower or the upper arch.

Figure 6:
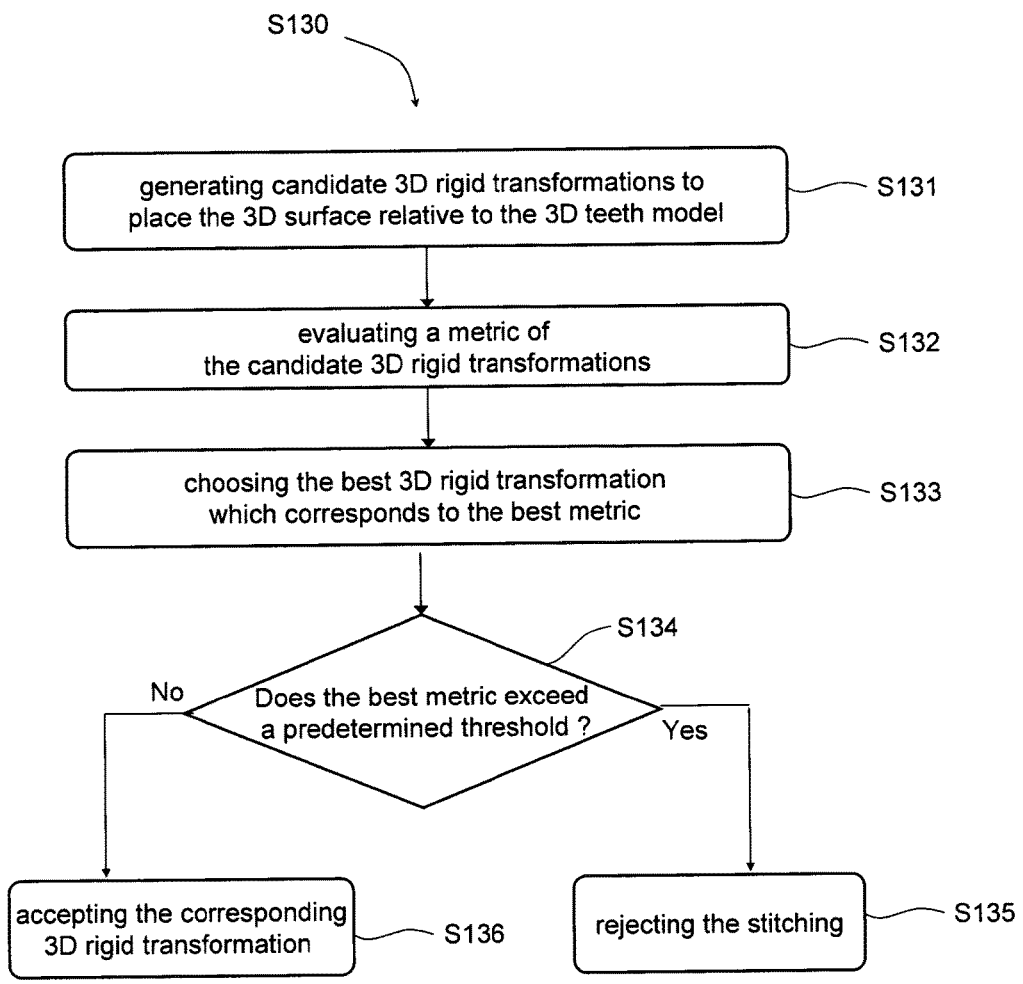
FIG. 6 is a schematic workflow of aligning the 3D teeth models with the bite surface in accordance with an embodiment of the invention.

FIG. 6 is a schematic workflow of aligning the 3D teeth models with the bite surface in accordance with an embodiment of the invention. The stitching of a portion of 3D teeth surface of the bite surface with the 3D teeth models includes steps of S131 to S136. In S131, generating candidate 3D rigid transformations to place the 3D teeth surface of the bite surface relative to the 3D teeth model. In S132, evaluating a metric of the candidate 3D rigid transformations using the relative placement of the 3D teeth surface relative to the 3D teeth model. In S133, choosing the best 3D rigid transformation which corresponds to a best metric. In S134, judging whether the best metric exceeds a predetermined threshold or not; if the best metric goes below a predetermined threshold, entering into S136 of accepting the corresponding 3D rigid transformation; if the best metric exceeds a predetermined threshold, entering into S137 of rejecting the stitching, which means a failure of stitching.

It is noted that the stitching process can be completed in a manual way, a semi-automatic way or automatic way. In case of using a semi-automatic way, the particular method of stitching can refer to U.S. Pat. No. 8,121,718 B2. In other preferred embodiment, the stitching process can be performed automatically based on an algorithm. The entire content of U.S. Pat. No. 8,121,718 B2 is incorporated by reference herein. It, can be understood that the automatic way used in aligning process could greatly save valuable time for user. Thus, not only the speed for bite registration but also the user experience is improved.

Further, in step of S140, judging whether the alignment in. S130 is successful or not. If the alignment is successful, coming into step of S150, i.e., the bite surface is displayed together with the 3D teeth models of the upper jaw and the lower jaw; if alignment is not successful, returning back to step of S120 so as to acquire another bite surface until the alignment is successful.

Figure 7:
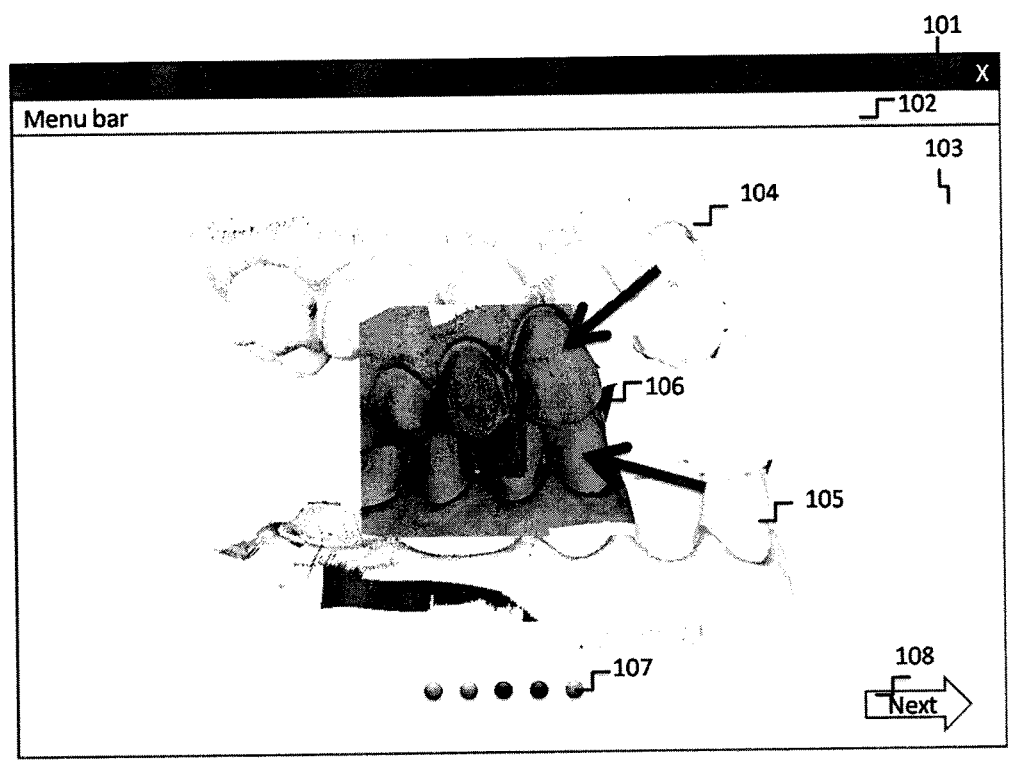
FIG. 7 shows a display of the user interface when succeeding to stitch in accordance with an embodiment of the invention.

FIG. 7 shows a display of the user interface when the alignment is successful in accordance with another embodiment of the invention. In an embodiment, as shown in FIG. 7, 106 denotes the bite surface together with the 3D teeth models of the upper/lower jaws stitched onto the bite surface, which represents one successful bite registration. Moreover, in particular, 101 denotes application window; 102 denotes application menu bar; 103 denotes application workspace; 104 denotes the 3D teeth model of the upper jaw in the initial placement; and 105 denotes the 3D teeth model of the lower jaw in the initial placement. The arrows represent a moving direction of the 3D teeth models of the upper/lower jaws in the process of alignment. When the alignment is successful, a transformation corresponding to the successful bite registration can be obtained and stored, and the user can employ it in the next step of computation of the final bite registration.

Figure 8:
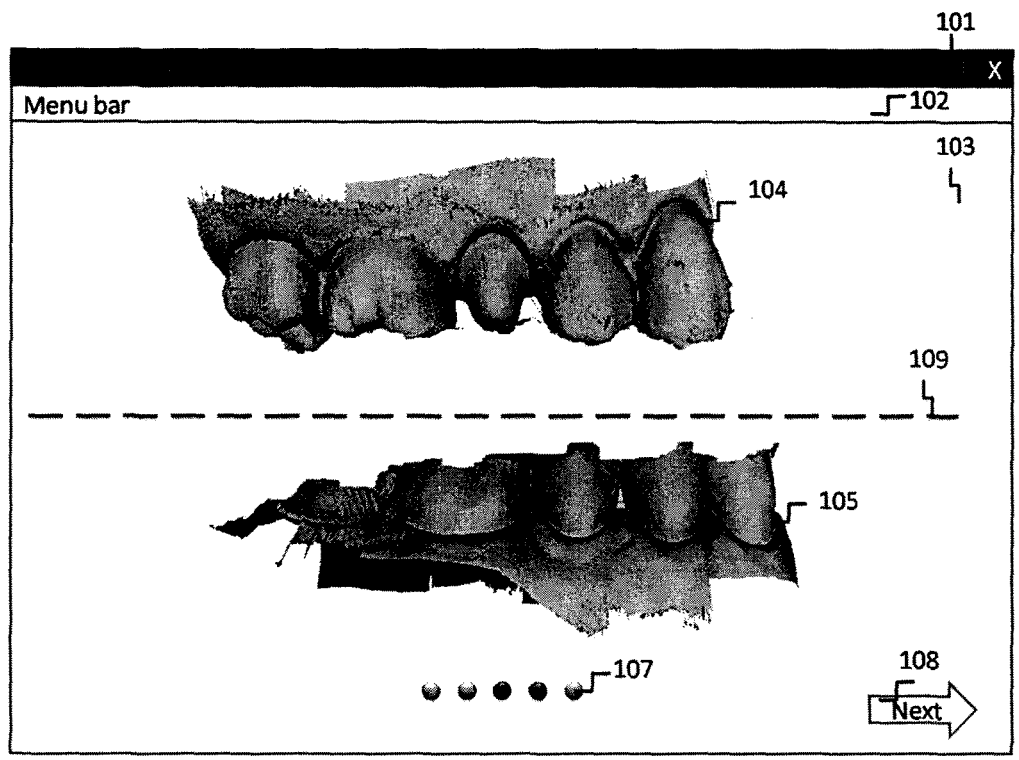
FIG. 8 shows a display of the user interface when not succeeding to stitch in accordance with another embodiment of the invention.

FIG. 8 shows a display of the user interface when the alignment is not successful in accordance with another embodiment of the invention. In case that the alignment is not successful, as shown in the user interface of FIG. 8, the user would receive a notification 109 of notification of failing to align or to register the bite surface. Moreover, the bite surface may be discarded automatically. Thus, the user only gets results which satisfy the algorithm quality criterion of alignment, which helps for improving the accuracy of bite registration. Meanwhile, it is necessary to return back to S120 so as to repeat anther circulated process of bite registration.

Further, in step of S160, the user can repeat to perform steps of S120 to S150 so as to obtain another successful bite registration. The time of repeating steps of S120 to S150 is not limited by this embodiment. The user can subjectively determine the time of repeating so as to obtain at least two successful bite registrations. A plurality of successful bite registrations can be stored and freely displayed by the user. Thus, it is very convenient to valuate all of successful bite registrations for the user, and the user can further select the ones with preferred transformation from successful bite registrations in the next step. As shown in FIG. 7 and FIG. 8, each button 107 represents a process of repeating. In an example, button 107 can be set as green color in case that the successful bite registration is selected.

Further, in step of S170, selecting at least one successful bite registration by evaluating at least two successful bite registrations. In this step, the bite surface with 3D models of the upper and lower jaws 106 can be displayed from different viewpoints; thus, this bite surface and the registered lower and upper arches may be observed from different viewpoints by the user, which greatly contributes to a full observation of the mismatch in different locations. When evaluating, the respective location of 3D teeth models of the upper jaw and the lower jaw can be evaluated by the user so as to judge whether the bite surface is suitable or not. If the mismatch corresponding to the distant end of the bite surface exceeds desired value, the bite surface and its corresponding bite registration are not suitable to be used in the next steps of computation of the final bite registration. For example, when the bite surface is selected from right side of molars, the user can observe the mismatch in the location of the left side of molars. Further by comparatively evaluating at least two successful bite registrations, one or more successful bite registrations and its corresponding bite surfaces with better evaluation results can be easily selected out by the user. Therefore, the user can select the bite registrations with optimized transformation in an intuitive way, which can further greatly improve the accuracy of the global 3D teeth model ultimately formed.

In particular, as shown in FIG. 7 and FIG. 8, the user can double-click any of the buttons 107 to enable and store desired successful bite registration and its corresponding bite surface, and the unselected one is disabled in the next steps of computation of the final bite registration. In one embodiment, when the successful bite registration is selected by the user, the button 107 turns green; when the successful bite registration is unselected the button 107 turns red. Thus, the user can easily distinguish the selected from the unselected successful bite registration. In another embodiment, the selection of the successful bite registration can be completed in an automatic way. In another embodiment, Step 170 automatically selects, all successful bite registration without user interaction. When further clicking button 108, going to step of S180.

Further, in step of S180, computing the final bite registration(s) using selected one or more successful bite registrations.

Figure 9:
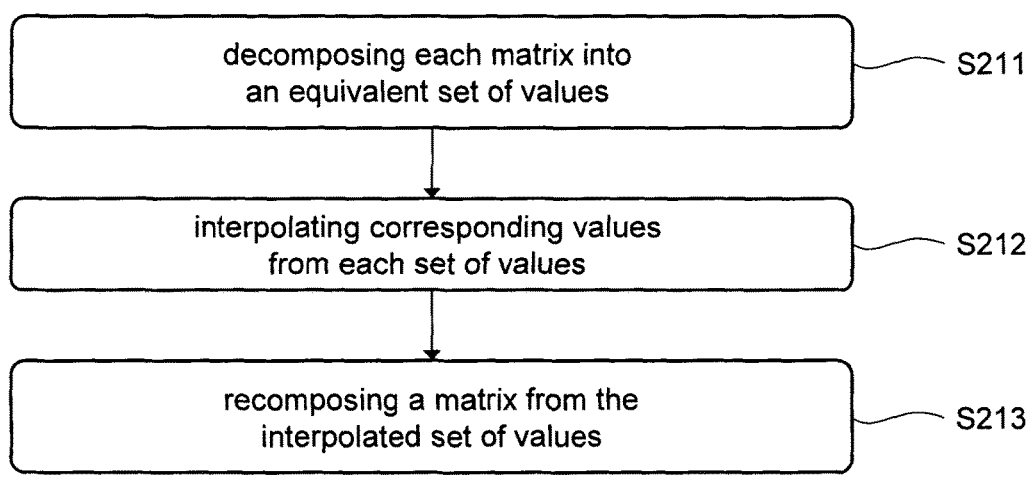
FIG. 9 shows a schematic workflow of multiple matrix interpolations.

In one embodiment, the computation of the final bite registration employs multiple matrix interpolation of the selected successful bite registrations. If at least two successful bite registrations are selected in step S170, combining all transformations corresponding to different selected successful bite registrations respectively into a single transformation. In particular, as shown in FIG. 9, a 4×4 matrix interpolation may contain the steps of decomposing each matrix into an equivalent set of values (S211), interpolating corresponding values from each set of values (S212) and recomposing a matrix from the interpolated set of values (S213). The set of equivalent values may consist in translation, scale, skew all represented as a vector with 3 components and perspective, quaternion both represented as a vector with 4 components. For detail, the abovementioned multiple matrix also described in interpolations are http://dev.w3.org/csswg/css3-transforms/#matrix-interpolation, and its disclosure can be incorporated by reference herein.

Therefore, in the embodiment of multiple matrix interpolation, S180 provides the user with a way to merge information from all selected bite registration together, and it can be seen as a process of averaging transformations (i.e. averaging the stitching noise) while keeping the upper and lower arches rigid.

It is noted that, if only one successful bite registration is selected in step S170, the transformation of the selected bite registration can be processed by a method of prior art.

In another embodiment, the computation employs the optimization of a cost function depending on the selected successful bite registrations, i.e., employs global matching of 3D views to simultaneously optimize relative placement of all views which have some overlay. The bite surface reused in this process is the bite surface corresponding to the selected bite registration. That is to say, the bite surface selected in the S170 is further used for optimizing the placement of each 3D surface.

To be specific, global matching refers to the placement optimization of each 3D surface so as to optimize a cost function. In an embodiment of global matching, 3D surfaces from the upper jaw, the lower jaw and selected successful bite registrations might be used altogether in the cost function to be optimize. In another embodiment of the global matching, a subset of 3D surfaces from the lower jaw, a subset of surfaces from the upper and a subset of selected successful bite registrations are used in the cost function to be optimized. In one embodiment, the cost function is computed from the distance between pairs of 3D surfaces. The distance between pairs of 3D surfaces might be computed from the distance between corresponding closest points on the surfaces. If the surfaces use a discrete representation, the corresponding points may be obtained using interpolation of the discrete coordinates. The distances between corresponding closest points on the surface may be weighted, and the weight might depend on a predetermined threshold. The predetermined threshold might represent a threshold distance above which influence of corresponding closest points decreases.

The cost function for a single pair of 3D surfaces S1 and S2 might be written:

$$f(S_1, S_2) = \sum_{i \in S_1} w_i d_i^2(S_1, S_2)$$

Where index i is a point on the surface $S_1$ and $d_i(S_1,S_2)$ the distance of that point to the other surface, and $w_i$ is a weight, which may depend on the initial distance between the two surfaces and also on a pre-determined threshold The cost function for all pairs of 3D surfaces may be written:

$$F = \sum_{k} \sum_{l \neq k} f(T_k(S_k), T_l(S_l))$$

Where (k,l) represents any pair of distinct surfaces and $T_k$, $T_l$ represent surfaces transformations to be optimized.

Global matching corresponds here to the minimization of a least square sum function where the unknowns are transforms $T_k$, $T_l$.

There exist other variations of a cost function which provide similar final transforms, which will be considered having the same role to those skilled in the art.

The optimization of a transform which uses the one or more selected bite registrations may refer to the placement optimization of the upper arch relative to the lower arch, using the one or more selected bite registrations by optimizing a cost function. In one embodiment, the cost function is computed from the distance between pairs of 3D surfaces. The distance between pairs of 3D surfaces might be computed from the distance between corresponding closest points on the surfaces. The distance between corresponding closest points on the surface may be weighted, and the weight might depend on a predetermined threshold. The predetermined threshold might represent, a threshold distance above which influence of corresponding closest points decreases.

The cost function for optimization of the transform may be written:

$$G = \sum_{b \in B} \sum_{l \in L} f(T_b(S_b), T(S_l)) + \sum_{b \in B} \sum_{u \in U} f(T_b(S_b), S_u)$$

Where b represents the index of a selected bite surface, B the pool of selected bite surface indices, L the pool of surfaces from the lower jaw, U the pool of surfaces from the upper jaw, $T_b$ the transform of each bite surface with index b, T the transform of the lower jaw relative to the upper jaw. The upper jaw is considered static in this representation, but there exist variations of this cost function which provide similar final transformations. The unknowns to be optimized are the individual transformations of bite surfaces $T_b$ and the global transformation of the lower jaw T.

Figure 10:
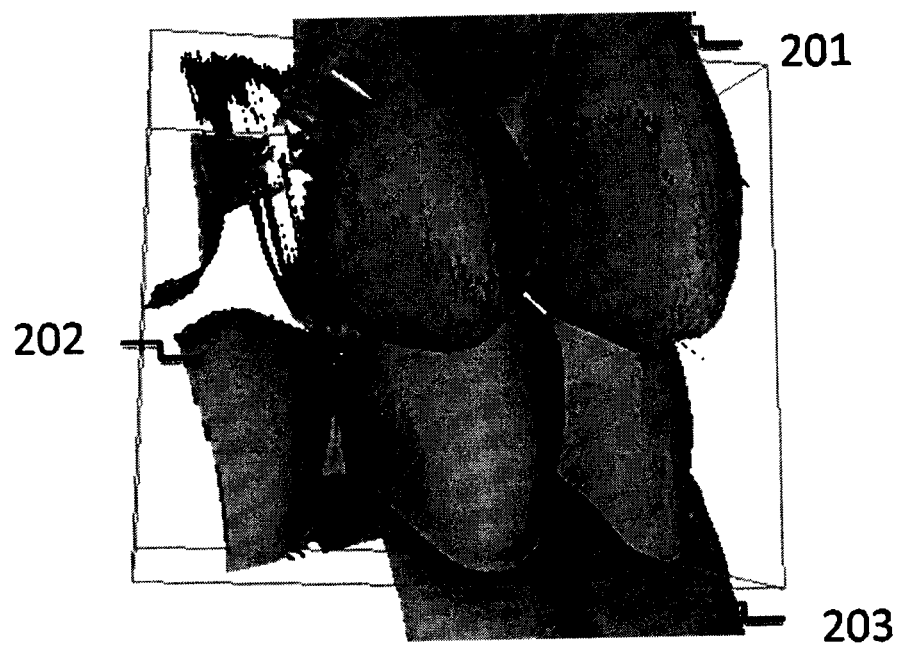
FIG. 10 shows a part of acquired 3D surface with the bite surface.

FIG. 10 shows a part of acquired 3D surface with the bite surface. Wherein, 201 denotes the upper jaw, 203 denotes the lower jaw, and 202 denotes the bite surface 202. The accumulated placement error from the upper and lower jaws is reduced by optimizing the placement of all meshes simultaneously. Thus, the relationship between upper and lower jaws is maintained and the placement of the meshes gets optimized.

After S220, the method for constructing a global 3D teeth model can further comprise other steps such as S230 of merging of meshes in lower jaw and in upper jaw separately to generate a global surface by interpolating surfaces in overlapping region, and S240 of meshing post-processing which combines mesh operations like hole-filling, smoothing, and cleaning. Other steps are known those skilled in the art, thus they are not carefully described herein.

Lastly, the global 3D teeth model is formed and displayed in the monitor. As using the accurate bite registration and steps of S210, and S220, the accuracy of the global 3D teeth model is greatly improved.

It can be understood that the system for bite registration can be seen as a sub-module of the system for constructing a global 3D teeth model.

In this context, a surface corresponds to surface acquired in one acquisition (also named one view) and may actually contain several disconnected surfaces.

The above examples mainly discuss the method and system for bite registration and the method and system for constructing a global 3D teeth model. While only some of the embodiments of the invention have been described, it is understood by those skilled in the art that the invention can be implemented in many other forms without departing from the spirit and scope thereof. Therefore, the illustrated examples and embodiments should be construed as exemplary rather than limiting. The invention may cover various modifications and replacements without departing from the spirit and scope of the invention as defined by appended claims.

The invention claimed is:

1. A method of bite registration, comprising the steps of:
   a. generating 3-dimensional (3D) teeth models of the upper jaw and the lower jaw;
   b. acquiring a bite surface containing a portion of at least one tooth of the upper jaw and a portion of at least one opposing tooth of the lower jaw simultaneously in a clenched state where the upper jaw is static relative to the lower jaw;
   c. attempting to align the 3D teeth models of the upper jaw and the lower jaw with the bite surface;
   d. displaying the bite surface together with the 3D teeth models of the upper jaw and the lower jaw aligned with the bite surface if alignment is successful;
   e. repeating step b to step d so as to obtain at least two successful bite registrations corresponding to different displayed bite surfaces;
   f. selecting two or more successful bite registrations by evaluating the at least two successful bite registrations and selecting said two or more of the displayed successful bite registrations; and
   g. computing a final bite registration between the teeth models of the upper jaw and the lower jaw using the selected two or more displayed successful bite registrations, and wherein in step e, when repeating to perform step b, the location of the acquired bite surface is changed.

2. The method of bite registration according to claim 1, wherein
   the computation of the final bite registration involves the optimization of a cost function depending on the selected successful bite registrations.

3. The method of bite registration according to claim 1, wherein
   the computation of the final bite registration involves one or more matrix interpolations of the selected successful bite registrations.

4. The method of bite registration according to claim 3, wherein said one or more interpolations contain steps of:
   decomposing each matrix into an equivalent set of values;
   interpolating corresponding values from each set of values; and
   recomposing a matrix from the interpolated set of values.

5. The method of bite registration according to claim 1, wherein step a includes the steps of:
   a1) capturing 3D teeth surface on the upper jaw or lower jaw by a scanner;
   a2) judging whether the captured 3D teeth surface is the first one or not during the scan;
   a3) if the captured portion is the first one, accepting the captured 3D teeth surface; and if further succeeding to accept, combining the captured 3D teeth surface with the 3D teeth model; and
   a4) if the captured portion is not the first one, attempting to stitch the captured 3D teeth surface onto the existing 3D teeth model; if succeeding to stitch, combining the captured 3D teeth surface with the existing 3D teeth model.

6. The method of bite registration according to claim 1, wherein step d including step of:
   if the alignment is not successful, the bite surface is discarded and the user receives a notification of failing to align or to register the bite surface, wherein if the alignment is not successful, automatically returning back to step b until the alignment is successful.

7. The method of bite registration according to claim 1, wherein the alignment is completed at least by stitching of a portion of 3D teeth surface of the bite surface with the 3D teeth models of the upper jaw and the lower jaw, where the bite surface includes a tooth of the upper jaw and an opposing tooth of the lower jaw.

8. The method of bite registration according to claim 1, wherein the alignment can be completed at least by stitching of a portion of 3D teeth surface of the acquired bite surface with either the lower or the upper arch, wherein the stitching process includes the steps of:
   generating candidate 3D rigid transformations to place the 3D teeth surface relative to the 3D teeth model;
   evaluating a metric of the candidate 3D rigid transformations using the relative placement of the 3D teeth surface relative to the 3D teeth model;
   choosing the best 3D rigid transformation which corresponds to a best metric; and
   if the best metric goes below a predetermined threshold, accepting the corresponding 3D rigid transformation; if the best metric exceeds a predetermined threshold, rejecting the stitching.

9. The method of bite registration according to claim 1, wherein the teeth contained in the bite surface are selected from incisors, premolar or molars.

10. The method of bite registration according to claim 1, wherein the bite surface is acquired based on one or more bite views captured by a scanner.

11. The method of bite registration according to claim 1, wherein the alignment is completed in a manual way, a semi-automatic way or automatic way.

12. The method of bite registration according to claim 1, wherein the final bite registration is used to construct a global 3D teeth model.

13. A system for bite registration, comprising:
   means for generating 3D teeth models of the upper jaw and the lower jaw;
   means for acquiring a bite surface containing a portion of at least one tooth of the upper jaw and a portion of at least one opposing tooth of the lower jaw simultaneously;
   means for attempting to align the 3D teeth models of the upper jaw and the lower jaw with the bite surface;
   means for displaying the bite surface together with the 3D teeth models of the upper jaw and the lower jaw aligned with the bite surface if alignment is successful;
   means for obtaining at least two successful bite registrations corresponding to different displayed bite surface by repeating;
   means for selecting two or more successful bite registrations by evaluating at least two successful bite registrations and selecting said two or more of the displayed successful bite registrations; and
   means for computing a final bite registration between the teeth models of the upper jaw and the lower jaw using the selected two or more displayed successful bite registrations, and wherein in the means for obtaining, the location of the acquired bite surface is changed,
   computing a final bite registration between the teeth models of the upper jaw and the lower jaw using the selected two or more displayed successful bite registrations, and wherein in step e, when repeating to perform step b, the location of the acquired bite surface is changed.

14. The system for bite registration according to claim 13, wherein the computation of the final bite registration involves the optimization of a cost function depending on the selected successful bite registrations.

15. The system for bite registration according to claim 13, wherein means for computing the final bite registration involves device for one or more matrix interpolations of the selected successful bite registrations.

16. The system for bite registration according to claim 15, wherein device for one or more matrix interpolations includes:
   module for decomposing each matrix into an equivalent set of values;
   module for interpolating corresponding values from each set of values; and
   module for recomposing a matrix from the interpolated set of values.

17. The system for bite registration according to claim 13, wherein means for attempting to align the 3D teeth models includes:
   module for, if the alignment is not successful, discarding the bite surface and sending a notification of failing to align to the user.

18. A system for bite registration, including a scanner and a computerized workstation, wherein the workstation is configured as:
   obtaining 3D teeth models of the upper jaw and the lower jaw, generated respectively, by the scanner;
   acquiring a bite surface containing a portion of at least one tooth of the upper jaw and a portion of at least one opposing tooth of the lower jaw simultaneously in a clenched state where the upper jaw is static relative to the lower jaw;
   attempting to align the 3D teeth models of the upper jaw and the lower jaw with the bite surface at the workstation;
   displaying the bite surface together with the 3D teeth models of the upper jaw and the lower jaw aligned with the bite surface if alignment is successful;
   repeating steps acquiring to step of displaying so as to obtain at least two successful bite registrations corresponding to different displayed bite surfaces;
   selecting two or more successful bite registrations by evaluating at least two successful bite registrations; and
   computing a final bite registration using the selected two or more successful bite registrations, and where in the repeating step, when repeating to perform the acquiring step, the location of the acquired bite surface is changed.

19. The system for bite registration according to claim 18, wherein the system is used to construct a global 3D teeth model.

20. A method of bite registration, characterized by comprising the steps of:
   a. generating 3-dimensional (3D) teeth models of the upper jaw and the lower jaw;
   b. acquiring a bite surface containing a part of at least one tooth of the upper jaw and a part of at least one opposing tooth of the lower jaw, simultaneously;
   c. attempting to align the 3D teeth models of the upper jaw and the lower jaw with the bite surface;
   d. displaying the bite surface together with the 3D teeth models of the upper jaw and the lower jaw aligned with the bite surface if alignment is successful;
   e. repeating step b to step d so as to obtain at least two successful bite registrations corresponding to different displayed bite surfaces;
   f. selecting one or more successful bite registrations by evaluating at least two successful bite registrations; and
   g. computing a final bite registration using selected one or more successful bite registrations, wherein the computation of the final bite registration involves one or more matrix interpolations of the selected successful bite registrations.

21. A method of bite registration, comprising:
   a. generating 3-dimensional (3D) teeth models of the upper jaw and the lower jaw;
   b. acquiring a bite surface containing a portion of the upper jaw and an opposing portion of the lower jaw simultaneously in a clenched state where the upper jaw is static relative to the lower jaw;
   c. attempting to align the 3D teeth models of the upper jaw and the lower jaw with the bite surface to achieve successful alignment;
   d. displaying the 3D teeth models of the upper jaw and the lower jaw aligned with the bite surface where successful alignment is achieved;
   e. repeating step b to step d so as to obtain at least two successful bite registrations corresponding to different displayed bite surfaces;
   f. selecting two or more successful bite registrations by evaluating the at least two successful bite registrations and selecting said two or more of the displayed successful bite registrations; and
   g. computing a final bite registration between the teeth models of the upper jaw and the lower jaw using the selected two or more displayed successful bite registrations, and wherein in step e, when repeating to perform step b, the location of the acquired bite surface is changed.

* * * * *